United States Patent [19]

Fauran et al.

[11] 4,072,682
[45] Feb. 7, 1978

[54] NEW 1-(2'-AROYL ETH-1' YL) 2-(4"-ACETAMIDO PIPERAZINE-1" YL METHYL) BENZIMIDAZOLES, THEIR THERAPEUTICAL APPLICATIONS AND METHOD FOR THEIR PREPARATION

[75] Inventors: Claude P. Fauran; Michel J. Turin, both of Paris; Thierry F. Imbert, La Celle Saint-Cloud; Guy M. Raynaud; Nicole A. M. Dorme, both of Paris, all of France

[73] Assignee: Delalande S.A., Courbevoie, France

[21] Appl. No.: 643,490

[22] Filed: Dec. 22, 1975

[30] Foreign Application Priority Data

Jan. 10, 1975 France .................. 75 00724

[51] Int. Cl.$^2$ ............................ C07D 241/04
[52] U.S. Cl. .................. 260/268 BC; 260/326.16; 424/250; 260/243.3; 548/327; 548/330; 544/121; 424/248.51; 424/248.57
[58] Field of Search .................. 260/268 BC, 326.16, 260/309.2; 424/273

[56] References Cited
U.S. PATENT DOCUMENTS

| 2,935,514 | 5/1960 | Hoffmann et al. .................. 424/273 |
| 3,325,356 | 6/1967 | DiNetta et al. .................. 424/273 |
| 3,505,354 | 4/1970 | Doebel et al. .................. 260/326.16 |

FOREIGN PATENT DOCUMENTS

1,216,381 12/1970 United Kingdom .......... 260/268 BC

*Primary Examiner*—Donald G. Daus
*Assistant Examiner*—D. B. Springer
*Attorney, Agent, or Firm*—Blanchard, Flynn, Thiel, Boutell & Tanis

[57] ABSTRACT

Compounds of the formula

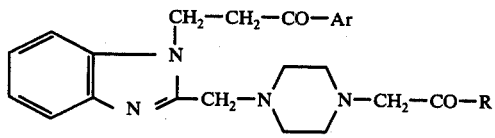

where
Ar is phenyl, substituted phenyl, α-furyl or α-thienyl, and
R is $NH_2$, $NHR^1$ wherein $R^1$ is alkyl or cycloalkyl, or $NR_1R_2$
wherein $R_1$ and $R_2$ are alkyl or —$N_1R_1R_2$ is piperidino, pyrrolidino, morpholino or hexamethyleneimino. The compounds are prepared by reacting the corresponding Ar-substituted chloromethylated benzimidazole with the corresponding R-substituted piperazine. The compounds possess gastric antisecretory, anti-ulcerous, spasmolytic, anti-cholinergic, anti-bronchoconstrictive, analgesic, anti-inflammatory, anti-hypertensive and diuretic properties.

4 Claims, No Drawings

NEW 1-(2'-AROYL ETH-1' YL) 2-(4"'-ACETAMIDO PIPERAZINE-1" YL METHYL) BENZIMIDAZOLES, THEIR THERAPEUTICAL APPLICATIONS AND METHOD FOR THEIR PREPARATION

The present invention concerns 1-(2'-aroyl eth-1' yl) 2-(4"'-acetamido piperazine-1" yl methyl) benzimidazoles, their method of preparation and their application in therapeutics.

the compounds of the invention correspond to the following general formula (I):

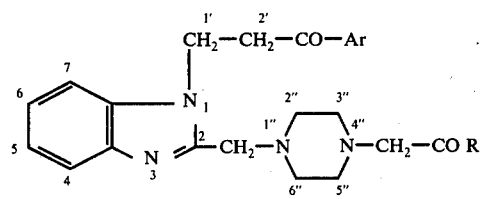

in which
Ar designates
  a phenyl nucleus which may be substituted by methoxy alkyl having 1 to 4 carbon atoms, nitro, or halogen, or
  α-furyl or α-thienyl, and
R designates
  —NH$_2$
  NHR' where R' is alkyl having from 1 to 4 carbon atoms, or cycloalkyl having at least 6 carbon atoms, or
  NR$_1$R$_2$ where R$_1$ and R$_2$ designate an alkyl group having 1 to 4 carbon atoms or form together with the nitrogen atom to which they are linked, a heterocyclic radical chosen from piperidino, pyrrolidino, morpholino and hexamethyleneimino.

The method of the invention consists of condensing a compound of formula (II):

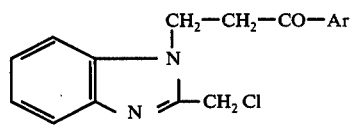

where Ar has the same significance as in formula (I), with a piperazine of formula (III):

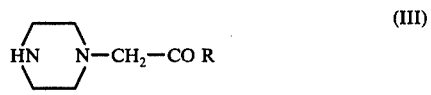

in which R has the same significance as in formula (I).

This condensation is effected in an ethyl acetate medium and in the presence of sodium carbonate.

The compounds of formula (II) are obtained by reacting an alcohol of formula (IV):

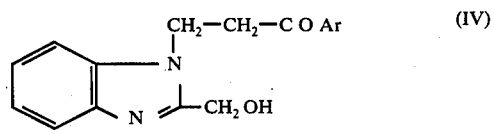

where Ar has the same significance as in formula (I), with thionyl chloride of formula (V): SO Cl$_2$ — (V) the preparation of the derivatives of formula (IV) being described in French application No. 72.19540 published under the No. 2 186 251.

The following preparations are given as examples to illustrate the invention.

EXAMPLE 1

1-(2'-benzoyl eth-1' yl) 2-(4"'-N-isopropylacetamido piperazine-1" yl) benzimidazole diamaleate. Code number : 73 0442

1st step : 1-(2'-benzoyl eth-1' yl) 2-(chloromethyl) benzimidazole. code number : 72 370

To a suspension of 0.62 mole of 1-(2'-benzoyl ethyl) 2-methanol benzimidazole in 480 ml of chloroform was added, at 15° C and within 1 hour, a solution of 0.95 mole of thionyl chloride in 270 ml of chloroform. After contacting for 2 hours at room temperature, the excess thionyl chloride was evaporated and the methanol solution of the chlorhydrate was neutralized with sodium bicarbonate. After filtration and evaporation, the crude base was recrystallized in ethyl acetate.

Melting point : 109° C
Yield : 67%
Empirical formula : C$_{17}$H$_{15}$Cl N$_2$O
Elementary analysis

|  | C | H | N |
|---|---|---|---|
| Calculated (%) | 68.34 | 5.06 | 9.38 |
| Obtained (%) | 68.14 | 5.18 | 9.24 |

2nd step : 1-(2'-benzoyl eth-1' yl) 2-(4"-N-isopropyl-acetamido piperazine-1" yl) benzimidazole dimaleate. Code number : 73 0442

To a suspension of 0.1 mole of 1-(2' benzoyl-eth-1' yl) 2-(chloromethyl) benzimidazole obtained in the previous step, in 250 ml of ethyl acetate, was added 0.15 mole of sodium carbonate then 0.12 mole of 1-(N-isopropylacetamido) piperazine. After a reflux of 6 hours, the reaction medium was taken up with 600 ml of water. The organic phase was decanted, then dried. After evaporation of the ethyl acetate, the crude mass was salified in 200 ml of acetone by means of maleic acid.

Melting point : 151° C
Yield : 82%
Empirical formula : C$_{34}$H$_{41}$N$_5$O$_{10}$
Elementary analysis

|  | C | H | N |
|---|---|---|---|
| Calculated (%) | 60.08 | 6.08 | 10.30 |
| Obtained (%) | 59.90 | 6.08 | 10.45 |

EXAMPLE 2

1-(2'-benzoyl eth-1' yl) 2-(4"-pyrrolidinocarbonylmethyl piperazine-1" yl methyl) benzimidazole. Code number : 73 0458

To a suspension of 0.1 mole of 1-(2'-benzoyl eth-1' yl) 2-(chloromethyl) benzimidazole obtained in the first step of example 1, in 250 ml of ethyl acetate was added 0.15 mole of sodium carbonate, then 0.12 mole of 1-pyrrolidinocarbonylmethyl piperazine. After a reflux of 1 hour, the sodium carbonate was separated by filtration and the ethyl acetate phase was concentrated.

The crude base obtained was purified by recrystallization in ethanol.

Melting point : 196° C
Yield : 80%
Empirical formula : $C_{27}H_{33}N_5O_2$
Elementary analysis

|  | C | H | N |
|---|---|---|---|
| Calculated (%) | 70.56 | 7.24 | 15.24 |
| Obtained (%) | 70.58 | 7.38 | 15.40 |

The compounds shown in table I following were prepared according to the operating mode of the second step of example 1.

TABLE I

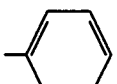  (I)

| Code number | Ar | R | Empirical formula | Molecular weight | Melting point (° C) | Yield (%) | Elementary analysis | | | |
|---|---|---|---|---|---|---|---|---|---|---|
| | | | | | | | | C | H | N |
| 74 0145 | 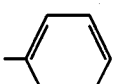 | —NH $CH_3$ | $C_{32}H_{37}N_5O_{10}$ | 651.66 | 152 | 69 | Calculated (%)<br>Obtained (%) | 58.98<br>58.68 | 5.72<br>5.85 | 10.75<br>10.59 |
| 74 0144 | 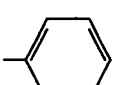 | —NH $C_2H_5$ | $C_{33}H_{39}N_5O_{10}$ | 665.69 | 142 | 90 | Calculated (%)<br>Obtained (%) | 59.54<br>59.50 | 5.91<br>5.92 | 10.52<br>10.65 |
| 74 0159 | 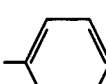 | —NH $C_3H_{7(n)}$ | $C_{34}H_{41}N_5O_{10}$ | 679.71 | 128 | 50 | Calculated (%)<br>Obtained (%) | 60.08<br>60.07 | 6.08<br>6.24 | 10.30<br>10.10 |
| 74 0186 | 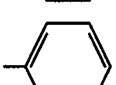 | —NH $C_4H_{9(n)}$ | $C_{35}H_{43}N_5O_{10}$ | 693.73 | 132 | 67 | Calculated (%)<br>Obtained (%) | 60.59<br>60.63 | 6.25<br>6.41 | 10.10<br>10.04 |
| 74 0187 | 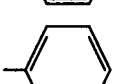 | —NH $C_4H_{9(i)}$ | $C_{35}H_{43}N_5O_{10}$ | 693.73 | 137 | 71 | Calculated (%)<br>Obtained (%) | 60.59<br>60.79 | 6.25<br>6.24 | 10.10<br>10.05 |
| 74 0180 | 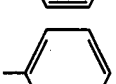 | —N $(CH_3)_2$ | $C_{33}H_{39}N_5O_{10}$ | 665.69 | 170 | 86 | Calculated (%)<br>Obtained (%) | 59.54<br>59.36 | 5.91<br>5.78 | 10.52<br>10.30 |
| 74 0453 | 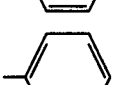 | —N $(C_3H_{7(i)})_2$ | $C_{37}H_{47}N_5O_{10}$ | 721.78 | 110 | 40 | Calculated (%)<br>Obtained (%) | 61.57<br>61.80 | 6.56<br>6.76 | 9.70<br>9.74 |
| 74 0184 | 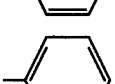 | —N $(C_2H_5)_2$ | $C_{35}H_{43}N_5O_{10}$ | 693.73 | 154 | 78 | Calculated (%)<br>Obtained (%) | 60.59<br>60.50 | 6.25<br>6.37 | 10.10<br>9.92 |
| 74 0196 |  | —N $(C_3H_{7(n)})_2$ | $C_{37}H_{47}N_5O_{10}$ | 721.79 | 143 | 78 | Calculated (%)<br>Obtained (%) | 61.57<br>61.63 | 6.56<br>6.80 | 9.70<br>9.65 |
| 74 0160 | 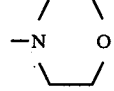 |  | $C_{35}H_{41}N_5O_{11}$ | 707.72 | 187 | 88 | Calculated (%)<br>Obtained (%) | 59.40<br>59.70 | 5.84<br>5.64 | 9.90<br>9.70 |
| 74 0195 | 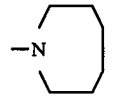 |  | $C_{37}H_{45}N_5O_{10}$ | 719.77 | 149 | 77 | Calculated (%)<br>Obtained (%) | 61.74<br>61.61 | 6.30<br>6.56 | 9.73<br>9.91 |
| 74 0655 | | —NH $C_4H_9(t)$ | $C_{35}H_{43}N_5O_{10}$ | 693.73 | 166 | 50 | Calculated (%)<br>Obtained (%) | 60.59<br>60.57 | 6.25<br>6.47 | 10.10<br>10.04 |

TABLE I-continued

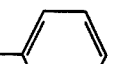
(I)

| Code number | Ar | R | Empirical formula | Molecular weight | Melting point (°C) | Yield (%) | Elementary analysis | | | |
|---|---|---|---|---|---|---|---|---|---|---|
| | | | | | | | | C | H | N |
| 74 0656 | 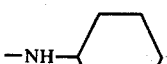 | —NH—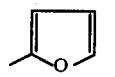 | $C_{37}H_{45}N_5O_{10}$ | 719.770 | 150 | 55 | Calculated (%) Obtained (%) | 61.74 61.47 | 6.30 6.57 | 9.73 9.60 |
| 74 0698 | 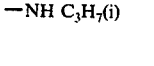 | —NH $C_3H_7(i)$ | $C_{32}H_{39}N_5O_{11}$ | 669.672 | 161 | 50 | Calculated (%) Obtained (%) | 57.39 57.24 | 5.87 5.73 | 10.46 10.26 |
| 74 0699 | 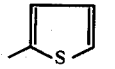 | —NH $C_3H_7(i)$ | $C_{32}H_{39}N_5O_{10}S$ | 685.738 | 170 | 62 | Calculated (%) Obtained (%) | 56.04 55.89 | 5.73 5.43 | 10.21 10.22 |
| 74 0700 | 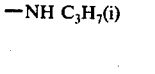 | —NH $C_3H_7(i)$ | $C_{35}H_{43}N_5O_{11}$ | 709.734 | 150 | 62 | Calculated (%) Obtained (%) | 59.23 59.31 | 6.11 6.07 | 9.87 9.79 |
| 75 0009 | 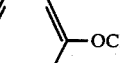 | —NH $C_3H_7(i)$ | $C_{35}H_{43}N_5O_{10}$ | 693.734 | 146 | 61 | Calculated (%) Obtained (%) | 60.59 60.44 | 6.25 6.24 | 10.10 10.11 |
| 75 0012 | 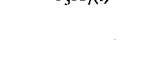 | —NH $C_3H_7(i)$ | $C_{34}H_{40}ClN_5O_{10}$, $H_2O$ | 732.157 | 151 | 45 | Calculated (%) Obtained (%) | 55.77 55.66 | 5.78 5.74 | 9.57 9.57 |
| 75 0010 | 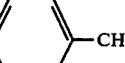 | —NH $C_3H_7(i)$ | $C_{35}H_{43}N_5O_{11}$ | 709.734 | 122 | 60 | Calculated (%) Obtained (%) | 59.23 58.93 | 6.11 6.31 | 9.87 9.78 |
| 75 0011 | 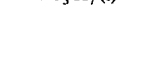 | —NH $C_3H_7(i)$ | $C_{35}H_{43}N_5O_{11}$ | 709.734 | 154 | 60 | Calculated (%) Obtained (%) | 59.23 59.00 | 6.11 6.14 | 9.87 9.87 |
| 75 0102 | 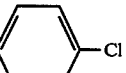 | —NH$_2$ | $C_{31}H_{35}N_5O_{10}$, 1,75 $H_2O$ | 669.158 | 140 | 50 | Calculated (%) Obtained (%) | 55.64 55.48 | 5.80 5.56 | 10.47 10.37 |
| 74 0751 | 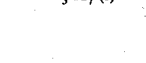 | —NH—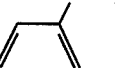 | $C_{36}H_{43}N_5O_{10}$ | 705.744 | 150 | 85 | Calculated (%) Obtained (%) | 61.26 61.01 | 6.14 6.10 | 9.92 9.70 |
| 74 0747 | 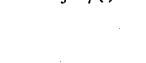 | —NH $C_3H_7(i)$ | $C_{34}H_{40}N_6O_{12}$ | 724.708 | 134 | 59 | Calculated (%) Obtained (%) | 56.34 56.18 | 5.56 5.64 | 11.60 11.43 |

The compounds of formula (I) were tested on laboratory animals and showed gastric antisecretory, anti-ulcerous, spasmolytic in vivo, anti-cholinergic and anti-bronchoconstrictive, analgesic, anti-inflammatory, anti-hypertensive and diuretic properties.

(1°) Gastric antisecretory properties

Administered intraduodenally to a rat, the compounds of formula (I) are capable of reducing gastric secretion measured after Shay ligature.

As examples, table II following gives the results obtained.

TABLE II

| Code No of tested compound | Dose administered (mg/kg/i.d.) | Reduction of volume of gastric secretion (%) |
|---|---|---|
| 75 0009 | 10 | 62 |
| 73 0458 | 2 | 19 |
| 75 0010 | 25 | 82 |
| 73 0442 | 2.1 | 68 |
| 75 0011 | 25 | 75 |
| 74 0145 | 1.6 | 88 |
| 75 0012 | 10 | 63 |
| 74 0144 | 1.6 | 85 |
| 75 0102 | 10 | 91 |
| 74 0159 | 1.5 | 77 |
| 74 0186 | 1.5 | 67 |
| 74 0187 | 1.5 | 78 |
| 74 0180 | 1.5 | 86 |

TABLE II-continued

| Code No of tested compound | Dose administered (mg/kg/i.d.) | Reduction of volume of gastric secretion (%) |
|---|---|---|
| 74 0184 | 1.5 | 77 |
| 74 0196 | 1.5 | 74 |
| 74 0160 | 1.5 | 45 |
| 74 0751 | 4.5 | 69 |

(2°) Anti-ulcerous properties

Compounds of formula (I), administered orally, reduce the area of ulcerations caused in a rat under stress for 7 hours.

Thus, table III gives the results obtained by administration of the different compounds of formula (I).

TABLE III

| Code No of tested compound | Dose administered (mg/kg/p.o.) | Percentage reduction of stress ulcers (%) |
|---|---|---|
| 73 0458 | 5 | 77 |
| 73 0442 | 5.2 | 99 |
| 74 0145 | 7.7 | 100 |
| 74 0144 | 7.7 | 99 |
| 74 0159 | 7.5 | 100 |
| 74 0186 | 7.4 | 98 |
| 74 0187 | 7.4 | 100 |
| 74 0180 | 7.7 | 100 |
| 74 0184 | 7.4 | 100 |
| 74 0196 | 7.3 | 88 |
| 74 0160 | 6 | 76 |
| 74 0195 | 7.1 | 59 |
| 75 0009 | 20 | 90 |
| 75 0010 | 20 | 77 |
| 75 0011 | 20 | 51 |
| 75 0012 | 20 | 64 |
| 75 0102 | 10 | 100 |

Furthermore, the compounds of formula (I) administered intraduodenally reduce the ulceration area caused by ligature of the pylorus of a rat (Shay's ulcers).

The results obtained are shown in table IV.

TABLE IV

| Code No of tested compound | Dose administered (mg/kg/i.d.) | Percentage reduction of Shay's ulcer (%) |
|---|---|---|
| 73 0458 | 10 | 90 |
| 75 0009 | 20 | 56 |
| 73 0442 | 7.6 | 88 |
| 75 0010 | 40 | 86 |
| 74 0145 | 15.5 | 100 |
| 75 0011 | 40 | 78 |
| 74 0144 | 15.5 | 98 |
| 75 0012 | 10 | 73 |
| 74 0159 | 15.1 | 100 |
| 75 0102 | 10 | 74 |
| 74 0186 | 14.8 | 75 |
| 74 0187 | 14.8 | 94 |
| 74 0180 | 7.7 | 94 |
| 74 0453 | 7.3 | 82 |
| 74 0184 | 7.4 | 100 |
| 74 0196 | 7.3 | 90 |
| 74 0160 | 15 | 99 |
| 74 0195 | 14.2 | 86 |
| 74 0751 | 10 | 89 |

(3°) Spasmolytic in vivo properties

The compounds of formula (I), administered intraduodenally are capable of reducing the contractions of the jejunal ansa of a rabbit, caused by electric stimulation.

The results obtained are shown in table V following:

TABLE V

| Code No of tested compound | Dose administered (mg/kg/i.d.) | Diminution of contraction of the jejunum for more than an hour - (%) |
|---|---|---|
| 75 0102 | 25 | 80 |
| 73 0442 | 26.5 | 67 |
| 74 0144 | 15.5 | 43 |
| 74 0180 | 15.4 | 50 |
| 74 0184 | 14.9 | 39 |

The same test was studied with the uterine horn of a female rabbit.

For example, compound No. 73.0442, administered at a dose of 53 mg/kg/i.d. reduces by 85% for more than an hour, the contractions of the uterine horn of a female rabbit caused by electric stimulation.

(4°) Anticholinergic and antibronchoconstrictive properties

Injected intravenously or intraduodenally, the compounds of formula (I) are capable of opposing bronchoconstriction caused in a guinea-pig by intravenous injection of acetylcholine and evaluated by Konzett's method. Table VI following shows the results obtained.

TABLE VI

| Code No of compound tested | Mode of administration | Dose administered (mg/kg) | Percentage inhibition of the bronchoconstriction (%) |
|---|---|---|---|
| 73 0458 | i.d. | 100 | 67 |
| 73 0442 | i.d. | 25 | 100 |
| 74 0145 | i.v. | 0.5 | 75 |
| 74 0144 | i.v. | 4 | 100 |
| 74 0159 | i.v. | 5 | 100 |
| 74 0186 | i.v. | 2 | 100 |
| 74 0187 | i.v. | 5 | 100 |
| 74 0180 | i.v. | 5 | 100 |
| 74 0453 | i.v. | 2.5 | 100 |
| 74 0184 | i.v. | 4 | 100 |
| 74 0195 | i.d. | 25 | 60 |

(5°) Analgesic properties

The compounds of formula (I), administered orally to a mouse, are capable of reducing the number of painful stretchings following intraperitoneal injection of acetic acid.

The results obtained are shown in table VII.

TABLE VII

| Code No of compound tested | Dose administered (mg/kg/p.o.) | Percentage diminution of the number of painful stretchings (%) |
|---|---|---|
| 73 0442 | 100 | 80 |
| 74 0145 | 10 | 70 |
| 74 0144 | 40 | 92 |
| 74 0159 | 50 | 40 |
| 74 0186 | 40 | 77 |
| 74 0187 | 50 | 42 |
| 74 0180 | 50 | 53 |
| 74 0184 | 50 | 63 |
| 74 0195 | 50 | 53 |

(6°) Anti-inflammatory properties

These properties are revealed, by a diminution following oral administration of the compounds of formule (I), of the local oedema caused in a rat by sub-plantar injection of a phlogenic agent, such as carragenine.

Table VIII gives as examples the results obtained with different compounds of formula (I).

TABLE VIII

| Code No of compound tested | Dose administered (mg/kg/p.o.) | Percentage reduction of sub-plantar oedema (%) |
| --- | --- | --- |
| 74 0145 | 10 | 40 |
| 74 0144 | 30 | 35 |
| 74 0159 | 50 | 57 |
| 74 0186 | 40 | 48 |
| 74 0187 | 50 | 47 |
| 74 0180 | 50 | 47 |
| 74 0184 | 50 | 65 |
| 74 0160 | 50 | 50 |

(7°) Anti-hypertensives properties

The compounds of formula (I) are capable, 4 hours after their oral injection, of bringing the arterial pressure down to normal in genetically hyperstressed vigil rats (S.H.R.).

Thus, administration of compounds No 750 011 and 740 747 respectively at doses of 10 mg/kg/p.o. and 150 mg/kg/p.o. are capable of bringing the arterial pressure down to normal in 4 animals out of 7.

(8°) Diuretic properties

The compounds of formula (I), administered orally to a rat, increase the volume of urine emitted, relative to controls, the volume being measured for the 6 hours following administration.

For example, compound 750 011 has a DE 50 equal to 1 mg/kg/p.o.

In addition, since the compounds of formula (I) are not very toxic, as can be seen from table IX following, the difference between pharmacologically active doses and lethal doses is sufficient, for these compounds, to permit their use in therapeutics.

TABLE IX

| Code No of compound tested | Lethal dose 50 (mouse) (mg/kg/p.o.) |
| --- | --- |
| 73 0458 | > 2 000 |
| 75 0009 | 1 800 |
| 73 0442 | 798 |
| 75 0010 | 1 200 |
| 74 0145 | 180 |
| 75 0011 | 120 |
| 74 0144 | 310 |
| 75 0012 | 1 300 |
| 74 0159 | 1 250 |
| 75 0102 | 1 300 |
| 74 0186 | 360 |
| 74 0187 | 1 600 |
| 74 0180 | 716 |
| 74 0453 | 1 000 |
| 74 0184 | 1 300 |
| 74 0196 | 2 100 |
| 74 0160 | 1 700 |
| 74 0195 | > 2 000 |
| 74 0751 | 1 100 |
| 74 0747 | 2 200 |

The compounds of formula (I) are principally indicated on the treatment of gastroduodenal ulcers, hyperchlorhydrias, visceral spasms, asthma, hypertension oedemas, pains of different, particularly inflammatory, origin.

They will be administered orally in the form of tablets, pills or gelules containing 25 to 200 mg of active ingredient (1 to 5 per day), in the form of drops containing 0.25 to 5% of active ingredient (10 to 40 drops - 1 to 3 times per day), parenterally in the form of injectable ampoules containing 5 to 150 mg of active ingredient (1 to 3 per day) and rectally in the form of suppositories containing 10 to 100 mg of active ingredient (1 to 3 per day).

The gastric antisecretory, anti-ulcerous and spasmolytic properties of different compounds according to the invention were compared with a reference compound will-known in its use in gastroenterology, diphemanil (methylsulfate).

(1°) Comparison of gastric antisecretory properties

| Compound tested | DL 50 (mouse) (mg/kg/p.o.) | Dose administered (mg/kg/i.d.) | Reduction of volume of gastric secretion - (%) | $\dfrac{\text{Dose adm.}}{\text{DL 50}} \, 10^3$ |
| --- | --- | --- | --- | --- |
| 73 0442 | 798 | 2.1 | 68 | 2.6 |
| 75 0009 | 1 800 | 10 | 62 | 5.5 |
| 74 0180 | 716 | 1.5 | 86 | 2.1 |
| 73 0458 | > 2 000 | 2 | 19 | < 1 |
| 74 0145 | 180 | 1.6 | 88 | 9 |
| 75 0010 | 1 200 | 25 | 82 | 21 |
| 74 0144 | 310 | 1.6 | 85 | 5.2 |
| 75 0012 | 1 300 | 10 | 63 | 8 |
| 74 0159 | 1 250 | 1.5 | 77 | 1.2 |
| 75 0102 | 1 300 | 10 | 91 | 8 |
| 74 0186 | 360 | 1.5 | 67 | 4.2 |
| 74 0751 | 1 100 | 4.5 | 69 | 4 |
| 74 0187 | 1 600 | 1.5 | 78 | 0.9 |
| 74 0184 | 1 300 | 1.5 | 77 | 1.2 |
| 74 0196 | 2 100 | 1.5 | 74 | 0.7 |
| 74 0160 | 1 700 | 1.5 | 45 | 0.9 |
| Diphemanil | 317 | 50 | 52 | 160 |

This table shows that the compounds of the invention present gastric antisecretory properties generally superior to diphemanil (methylsulfate) at substantially lower doses.

(2°) Comparison of anti-ulcerous properties

| Compound tested | DL 50 (mouse) (mg/kg/p.o.) | Dose administered (mg/kg/p.o.) | Percentage reduction of stress ulcers - (%) | $\frac{\text{Dose adm.}}{\text{DL 50}} \cdot 10^3$ |
| --- | --- | --- | --- | --- |
| 73 0442 | 798 | 5.2 | 99 | 6.5 |
| 75 0009 | 1 800 | 20 | 90 | 11 |
| 74 0180 | 716 | 7.7 | 100 | 11 |
| 75 0010 | 1 200 | 20 | 77 | 17 |
| 73 0458 | > 2 000 | 5 | 77 | < 2.5 |
| 74 0145 | 180 | 7.7 | 100 | 43 |
| 75 0011 | 120 | 20 | 51 | 170 |
| 74 0144 | 310 | 7.7 | 99 | 25 |
| 75 0012 | 1 300 | 20 | 64 | 15 |
| 74 0159 | 1 250 | 7.5 | 100 | 6 |
| 75 0102 | 1 300 | 10 | 100 | 8 |
| 74 1086 | 360 | 7.4 | 98 | 21 |
| 74 0751 | 1 100 | 11 (DE 50) | — | — |
| 74 0187 | 1 600 | 7.4 | 100 | 4.6 |
| 74 0184 | 1 300 | 7.4 | 100 | 5.7 |
| 74 0196 | 2 100 | 7.3 | 88 | 3.5 |
| 74 0160 | 1 700 | 6 | 76 | 3.5 |
| 74 0195 | > 2 000 | 7.1 | 59 | < 3.5 |
| Diphemanil | 317 | 100 | 91 | 315 |

This table shows that the compounds of formula (I) present anti-ulcerous properties very much superior the diphemanil since, administered at a dose such that the ratio dose administered/DL 50 is at least equal to 170, they bring about a percentage reduction of stress ulcers between 51 and 100%, whereas diphemanil administered at a dose such that the ratio dose administered/DL 50 is equal to 315 brings about a percentage reduction of 91%.

(3°) Comparison of spasmolytic in vivo properties

| Compound tested | DL 50 (mouse) (mg/kg/p.o.) | Dose administered (mg/kg/i.d.) | Diminution of contractions of the jejunum of a rabbit - (%) | $\frac{\text{Dose adm.}}{\text{DL 50}} \cdot 10^3$ |
| --- | --- | --- | --- | --- |
| 73 0442 | 798 | 26.5 | 67 | 33 |
| 74 0180 | 716 | 15.4 | 50 | 21 |
| 74 0144 | 310 | 15.5 | 43 | 50 |
| 74 0184 | 1 300 | 14.9 | 39 | 11 |
| 74 0195 | > 2 000 | 14.2 | 30 | < 7 |
| Diphemanil | 317 | 20 | 70 | 63 |

This comparison shows that the compounds according to the invention enable a spasmolytic effect in vivo to be obtained, at least equal to that resulting from the administration of diphemanil by administration of a dose representing a smaller fraction of the lethal dose.

This study then shows that the compounds of formula (I) provide an important technical progress as regards the prior art.

What we claim is:

1. A compound having the formula

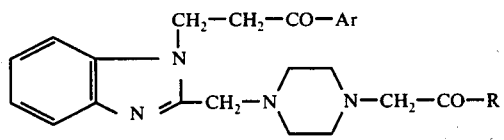

wherein Ar is α-furyl, α-thienyl, phenyl or phenyl substituted by one substituent selected from the group consisting of methoxy, alkyl having one to 4 carbon atoms, nitro and chloro, and R is —NH$_2$, —NHR$^1$ wherein R$^1$ is alkyl having one to four carbon atoms or cycloalkyl having 5 or 6 carbon atoms, or —NR$_1$R$_2$ wherein R$_1$ and R$_2$ are alkyls having one to 4 carbon atoms or —NR$_1$R$_2$ is piperidino, pyrrolidino or hexamethyleneimino, and the pharmaceutically acceptable acid addition salts thereof.

2. A compound according to claim 1 where Ar is phenyl, and R is selected from the group consisting of amino, methylamino, ethylamino, n-propylamino, n-butylamino, isopropylamino, iso-butylamino, tert.-butylamino, cyclopentylamino, cyclohexylamino, dimethylamino, di-n-propylamino, diethylamino, di-isopropylamino, pyrrolidino and hexamethyleneimino.

3. A compound according to claim 1 where R is isopropylamino, and Ar is selected from the group consisting of α-furyl, α-thienyl, p-methoxyphenyl, p-methylphenyl, p-chlorophenyl, o-methoxyphenyl, m-methoxyphenyl and p-nitrophenyl.

4. A compound as claimed in claim 1 in which Ar is phenyl and R is isopropylamino.

* * * * *